(12) United States Patent
Arumugam et al.

(10) Patent No.: US 9,926,250 B2
(45) Date of Patent: Mar. 27, 2018

(54) SYSTEM FOR REGENERATING MONO ETHYLENE GLYCOL AND A METHOD THEREOF

(71) Applicant: RELIANCE INDUSTRIES LIMITED, Mumbai (IN)

(72) Inventors: Anandan Arumugam, Chennai (IN); Mandava Subbarao, Vijayawada (IN); Adda Ramarao, Kakinada (IN); Ghadge Rajaram Shrimant, Navi Mumbai (IN); Natarajan Venkateswaran, Navi Mumbai (IN); Nemani Venkateswara Rao, Kakinada (IN); Mihir Mangal Pattnaik, Vishakhapatnam (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/321,951

(22) PCT Filed: Jun. 23, 2015

(86) PCT No.: PCT/IB2015/054688
§ 371 (c)(1),
(2) Date: Dec. 23, 2016

(87) PCT Pub. No.: WO2015/198212
PCT Pub. Date: Dec. 30, 2015

(65) Prior Publication Data
US 2017/0129835 A1     May 11, 2017

(30) Foreign Application Priority Data

Jun. 27, 2014 (IN) .......................... 2095/MUM/2014
Oct. 9, 2014 (IN) .......................... 2881/MUM/2014

(51) Int. Cl.
| | |
|---|---|
| *C07C 29/80* | (2006.01) |
| *B01D 3/00* | (2006.01) |
| *B01D 19/00* | (2006.01) |
| *B01D 21/00* | (2006.01) |
| *C07C 29/76* | (2006.01) |
| *B01D 3/06* | (2006.01) |
| *B01D 21/01* | (2006.01) |
| *B01D 21/24* | (2006.01) |
| *B01D 3/32* | (2006.01) |
| *B01D 21/26* | (2006.01) |

(52) U.S. Cl.
CPC ................ *C07C 29/80* (2013.01); *B01D 3/06* (2013.01); *B01D 3/32* (2013.01); *B01D 19/0036* (2013.01); *B01D 21/0012* (2013.01); *B01D 21/01* (2013.01); *B01D 21/245* (2013.01); *B01D 21/262* (2013.01); *C07C 29/76* (2013.01)

(58) Field of Classification Search
CPC .. C07C 29/80; B01D 3/06; B01D 3/32; B01D 19/0036; B01D 21/0012
USPC ........................................................ 568/868
See application file for complete search history.

(56) References Cited

U.S. PATENT DOCUMENTS 7,232,505 B2 *  6/2007  Laborie ................... C07C 29/76
                                                                       203/18

FOREIGN PATENT DOCUMENTS

| WO | 2010/080038 A1 | 7/2010 |
| WO | 2011/028131 A1 | 3/2011 |

OTHER PUBLICATIONS

International Search Report and Written Opinion for Application No. PCT/IB2015/054688, dated Aug. 10, 2015, 8 pages.

* cited by examiner

*Primary Examiner* — Sikarl A Witherspoon

(57) ABSTRACT

The present disclosure provides a system (100) for regenerating MEG, the system (100) comprising at least one flash drum (101) adapted to increase the temperature of rich MEG. At least one settling tank (102) is fluidly connected to the flash drum (101) where low solubility salts in the rich MEG are precipitated. Further, at least one filter unit (103) is fluidly connected to downstream of settling tank (102), and is configured to separate low solubility salt precipitates from the rich MEG. Furthermore, at least one storage tank (104) is positioned downstream of the filter unit (103), which is configured to receive and accumulate filtrate containing rich MEG. A reclamation column (105) is fluidly connected to the storage tank (104), which comprises a distillation chamber (106) and vane-mesh assembly (107) configured to produce lean MEG. The system (100) also has water handling capacity from 400 m³/day to 450 m³/day.

25 Claims, 2 Drawing Sheets

SYSTEM FOR REGENERATING MONO ETHYLENE GLYCOL AND A METHOD THEREOF

CROSS-REFERENCE TO RELATED APPLICATIONS

This application is a national phase application of International Application No. PCT/IB2015/054688, filed on Jun. 23, 2015, which claims priority to and benefits of Indian Patent Application No. 2095/MUM/2014 filed on Jun. 27, 2014 and Indian Patent Application No. 2881/MUM/2014, filed on Sep. 10, 2014. The contents of the above-referenced applications are incorporated herein by reference in their entirety.

TECHNICAL FIELD

The present disclosure generally relates to the field of recovery of hydrate inhibitors. Particularly, but not exclusively, the present disclosure relates to a system and method for regeneration of hydrate inhibitors. Further, embodiments of the disclosure disclose the system and method for regenerating Mono Ethylene Glycol which is used as hydrate inhibitor in oil and natural gas production plants.

BACKGROUND

Fossil fuels such as but not limiting to natural gas are formed deep inside the earth when layers of plants, animal matter and gases are exposed to intense heat and pressure for thousands of years. During transportation of these gases (along with formation water) from extraction wells to receiving facility such as onshore terminals, gas hydrates or clathrate hydrates are formed which tend to clog the flow lines such as pipes. The gas hydrates physically resemble ice and are formed due to entrainment of non-polar molecules (mostly gaseous molecules) in cages of hydrogen bonded water molecules to form crystalline water based solids, which cause blockages in flow lines. For many years, several hydrate inhibitors such as but not limiting to glycols and methanol have been used as primary chemical compounds to prevent blockages in pipe lines due to gas hydrate formation, and are usually injected into production fluids present in extraction wells.

Generally, onshore and offshore applications require persistent inhibition of hydrates, and hence, the cost of replacing hydrate inhibitor that is lost to the gas and liquid hydrocarbon product streams is a determining factor in selecting the inhibitor. Methanol solubility in gas and liquid hydrocarbon product streams may be two or more orders of magnitude higher than glycol solubility. This creates a strong economic motivation to use glycols such as but not limiting to Mono Ethylene Glycol (MEG), despite the greater quantity of MEG needed per degree of hydrate temperature suppression. However, the adoption of MEG over methanol has taken some time to occur, due in part to familiarity with methanol and owing to operating difficulties in recovering and recycling MEG.

Conventionally, MEG is used in hydrocarbon gas and/or condensate pipelines to absorb moisture and prevent gas hydrate formation in the pipeline, which otherwise can lead to blockage and corrosion. Typically, MEG (or other inhibitor) is injected into well fluids at a loading facility, and is separated from the well fluids at a receiving facility. The separated MEG (known as rich MEG), which carries absorbed water (containing formation water and condensed water) is regenerated by a water and salt removal process to produce "lean MEG" for re-use. The separated MEG also tends to become polluted by other components in the pipeline, such as pipeline corrosion products, dissolved gases, hydrocarbon condensates and salts. The salts are mainly present in formation water, and may separate by forming precipitates during the MEG regeneration process. Removal of these particles from MEG improves the performance of the MEG regeneration process, because the particles tend to accumulate in the regeneration process, and clogs process equipment. One known solution to this problem is to separate the particles by introducing a solid separation unit including but not limiting to a centrifuge in the MEG reclamation and regeneration plant.

Further, formation water present in rich MEG contains salts which include low solubility salts and high solubility salts. The low solubility salt precipitates include ingredients such as but not limiting to Calcium carbonate, Magnesium Hydroxide, Iron carbonate and so on, and are mostly divalent salts. Generally, some divalent cations like $Ca^{2+}$, $Fe^{2+}$, $Mg^{2+}$, etc undergo ionic bonding with divalent anions to form insoluble salts whose solubility decrease with increase in temperature. Hence, it is necessary that these divalent salts are removed from rich MEG so that they do not proceed further to reclamation unit where they are rendered insoluble, under certain process conditions, such as rise in temperature. The high solubility salts, on the other hand, include but not limiting to Sodium chloride, Potassium chloride etc, which are mostly monovalent salts. As the name implies, these salts have high degree of solubility and may be regarded as dissolved impurities present in rich MEG solution. Now, MEG has to be separated from water and salts (monovalent and divalent) for re-injecting back to wells through MEG Pre-treatment and Reclamation plant. Conventional MEG reclamation and regeneration plants comprise of a separation unit which receives mixture of MEG and fuel in liquid and/or gaseous state (called well fluids) from extraction wells, through one or more flow lines. The separation unit separates MEG solution from the gas, and gas is sent to dehydration unit for removal of moisture and thereafter for further processing. The separated MEG i.e. rich MEG is fed into the regeneration unit, and a small part of rich MEG containing supersaturated precipitates of both the salts (monovalent and divalent) are sent to a solid removal unit such as but not limiting to a centrifuge including but not limiting to a decanter type centrifuge. The solid separation unit separates the supersaturated salt precipitates from incoming streams, and thereby allows clear MEG to flow into the regeneration unit for further processing. In the regeneration unit, moisture content, i.e. water, is removed from the MEG to obtain MEG in its lean form which can be re-injected into extraction wells to continue the cycle.

The presence of salts, and most importantly the divalent salts in rich MEG solution poses problems such as formation of scales (scaling) in flow lines and tend to choke few units of the reclamation section, and mainly the chamber containing centrifuge. This creates a need for manual intervention to periodically clean the reclamation unit as well as the centrifuge. In addition, precipitates of divalent salts tend to corrode pipelines and cause suspension of corroded particles, thereby increasing the concentration of suspended impurities in the MEG solution. This increases load on the centrifuge and hampers its performance, which in turn hampers the performance of MEG Reclamation Plant. In addition, high vibration and torque are observed during centrifuge operation due to difference in feed water concentration and increase in temperature. Hence, the system shut down time is more, resulting in inefficient utilization of resources, which are undesirable. Another problem encountered during the process is producing high quality lean MEG solution, without compromising with quantity of water removed from the rich MEG solution. A MEG solution which has salinity less than 500 ppm is considered to be of high purity. However, with the increase in water handling capacity, finer salt particles would be carried with the MEG solution into the reclamation column, which again results in one or more limitations as explained above.

In addition to the above, the conventional MEG regeneration systems can handle water only up to 300 m$^3$/day. This results in reduction in efficiency of the system in terms of quality and quantity of regenerated MEG, which would inherently increase the process time and power consumption. However, if an attempt is made to increase the water handling capacity above 300 m$^3$/day in the conventional MEG regeneration systems, the salinity and conductivity of the regenerated MEG will be increased. This makes the MEG impure, and poses problems as stated above, making it unsuitable for re-injection into extraction wells.

In light of foregoing discussion, there is a need to develop an improved system and method for regenerating mono ethylene glycol to overcome the limitations stated above.

SUMMARY OF THE DISCLOSURE

One or more drawbacks of conventional hydrate inhibitor regeneration systems as described in background are overcome, and additional advantages are provided through the system and method as claimed in the present disclosure. Additional features and advantages are realized through the technicalities of the present disclosure. Other embodiments and aspects of the disclosure are described in detail herein and are considered to be a part of the claimed disclosure.

In one non-limiting embodiment of the present disclosure, there is provided a system for regenerating Mono Ethylene Glycol (MEG). The system comprising at least one flash drum adapted to receive rich mono ethylene glycol (MEG). The rich mono ethylene glycol (MEG) is heated to a predetermined temperature in the at least one flash drum. At least one settling tank is fluidly connected to the at least one flash drum, where low solubility salts present in the rich mono ethylene glycol (MEG) are precipitated. Further, at least one filter unit is fluidly connected to the at least one settling tank and is positioned downstream of the at least one settling tank. The at least one filter unit is configured to separate low solubility salt precipitates from the rich mono ethylene glycol (MEG). Furthermore, at least one storage tank is positioned downstream of the at least one filter unit, which is configured to receive and accumulate filtrate containing rich mono ethylene glycol (MEG) flowing out of the filter unit. A reclamation column is fluidly connected to the at least one storage tank, which comprises a distillation chamber configured to vaporize water present in the rich mono ethylene glycol (MEG) to produce lean mono ethylene glycol (MEG). In addition, the reclamation column comprises a vane-mesh assembly which is configured to separate fine solid particles from the vaporized mono ethylene glycol (MEG) and water. The system also comprises at least one centrifuge which is fluidly connected to the reclamation column and is configured to separate high solubility salts from the rich mono ethylene glycol (MEG). The system is configured to handle water from about 400 meter cube per day (m$^3$/day) to about 450 meter cube per day (m$^3$/day).

In an embodiment of the present disclosure, the mono ethylene glycol (MEG) is used as hydrate inhibitor during processing of liquid and gaseous hydrocarbon fuels.

In an embodiment of the present disclosure, the at least one separation unit is fluidly connected to the at least one flash drum and is configured to separate hydrocarbon fuel from rich mono ethylene glycol (MEG).

In an embodiment of the present disclosure, the predetermined temperature ranges from 75 degree celcius (° C.) to 85 degree celcius (° C.).

In an embodiment of the present disclosure, the at least one settling tank comprises of at least one overflow passage to allow flow of rich mono ethylene glycol (MEG) into the filter unit and at least one provision to receive chemical substances.

In an embodiment of the present disclosure, the chemical substances which are added to the settling tank convert low solubility salts present in rich mono ethylene glycol (MEG) into low solubility salt precipitates.

In an embodiment of the present disclosure, the at least one filter unit comprises of a first inlet fluidly connected to bottom of the at least one settling tank, a second inlet fluidly connected to the at least one storage tank, and a drain passage configured to discharge low solubility salt precipitates.

In an embodiment of the present disclosure, the at least one settling tank is fluidly connected to the at least one storage tank.

In an embodiment of the present disclosure, the vane-mesh assembly comprises of at least one vane pack and at least one mesh pack configured to filter the fine solid particles from the mono ethylene glycol (MEG).

In an embodiment of the present disclosure, the at least one vane pack of the vane-mesh assembly filters solid particles of size greater than 20 microns and the at least one mesh pack of the vane-mesh assembly filters solid particles of size greater than 10 microns.

In an embodiment of the present disclosure, at least one pump is fluidly disposed between the reclamation column and the at least one centrifuge, and is configured to circulate the rich mono ethylene glycol (MEG) between the reclamation column and the at least one centrifuge.

In an embodiment of the present disclosure, the water vaporized in reclamation column is discharged to effluent treatment plant.

In another non-limiting embodiment of the present disclosure, there is provided a method for regenerating mono ethylene glycol (MEG). The method comprises act of increasing temperature of rich mono ethylene glycol (MEG) by heating the rich mono ethylene glycol (MEG) in at least one flash drum. Further, the method comprises act of precipitating low solubility salts present in the rich mono ethylene glycol (MEG) in at least one settling tank which is fluidly connected to the at least one flash drum, and separating low solubility salt precipitates from the rich mono ethylene glycol (MEG) in at least one filter unit which is fluidly connected to the at least one settling tank. The at least one filter unit is positioned downstream of the at least one settling tank. The method also comprises act of accumulating filtrate containing rich mono ethylene glycol (MEG) flowing out of the at least one filter unit in at least one storage tank which is fluidly connected to the at least one filter unit, and is positioned downstream of the at least one filter unit. Then, routing the filtrate containing rich mono ethylene glycol (MEG) from the at least one storage tank to a reclamation column to obtain lean mono ethylene glycol (MEG). Obtaining the lean mono ethylene glycol (MEG)

from the reclamation column comprises steps of separating high solubility salts from the rich mono ethylene glycol (MEG) by at least one centrifuge fluidly connected to the reclamation column, vaporizing water present in the rich mono ethylene glycol (MEG) in a distillation chamber of the reclamation column and separating fine solid particles from the vaporized mono ethylene glycol (MEG) and water through a vane-mesh assembly of the reclamation column. The system is configured to handle water from 400 meter cube per day (m$^3$/day) to 450 meter cube per day (m$^3$/day).

In an embodiment of the present disclosure, the rich mono ethylene glycol (MEG) is heated to a temperature ranging from 75 degree celcius (° C.) to 85 degree celcius (° C.) in the at least one flash drum.

In an embodiment of the present disclosure, separation of high solubility salts and vaporization of water occur simultaneously.

In an embodiment of the present disclosure, the method comprises act of separating hydrocarbon fuel from the rich mono ethylene glycol (MEG) in at least one separation unit which is fluidly connected to the flash drum.

In an embodiment of the present disclosure, the method comprises act of increasing the temperature of rich mono ethylene glycol (MEG) to facilitate precipitation of low solubility salts in the settling tank and to separate fluidic impurities from the rich mono ethylene glycol (MEG).

In an embodiment of the present disclosure, the method comprises act of routing excess rich mono ethylene glycol (MEG) from the at least one settling tank to the at least one filter unit through at least one overflow passage.

In an embodiment of the present disclosure, the method comprises act of routing rich mono ethylene glycol (MEG) from the at least one storage tank to the at least one filter unit through at least one port.

In an embodiment of the present disclosure, the low solubility precipitates are formed by adding chemical substances to rich mono ethylene glycol (MEG) in the at least one settling tank.

It is to be understood that the aspects and embodiments of the disclosure described above may be used in any combination with each other. Several of the aspects and embodiments may be combined together to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF ACCOMPANYING FIGURES

The novel features and characteristics of the disclosure are set forth in the appended description. The disclosure itself, however, as well as a preferred mode of use, and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which.

Figure 1:
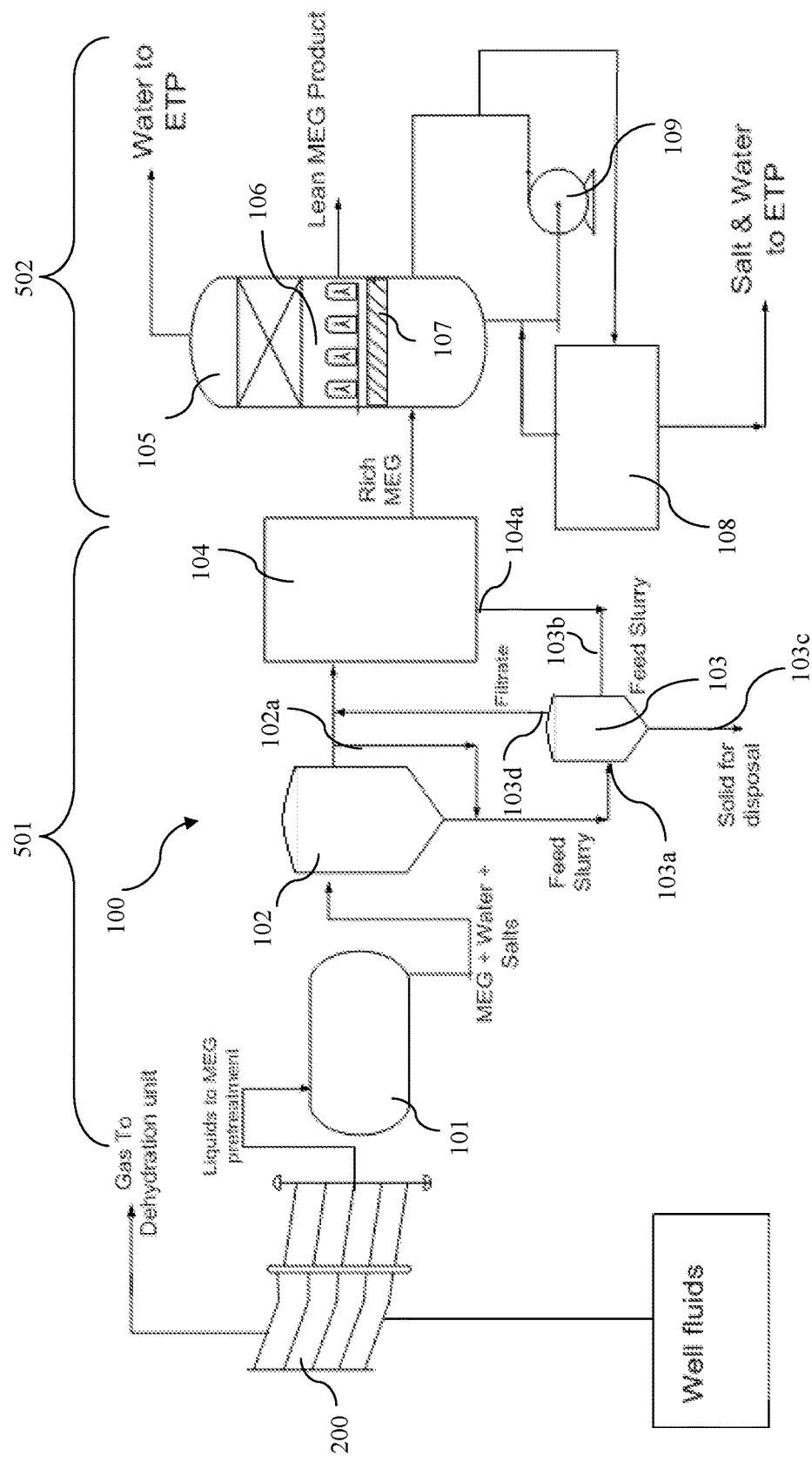
FIG. 1 illustrates a schematic view of the system used for regenerating mono ethylene glycol (MEG), according to an embodiment of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other systems for carrying out the same purposes of the present disclosure. It should also be realized by those skilled in the art that such equivalent constructions do not depart from the scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

To overcome one or more limitations stated in the background, the present disclosure provides a system and a method for regenerating mono ethylene glycol (MEG) from a mixture. Mono ethylene glycol is an organic compound which belongs to the family of glycols, having colorless, odourless, hygroscopic characteristics. It is used in variety of applications such as but not limiting to extraction and processing of hydrocarbon fuels in both liquid and gaseous states, such as crude petroleum and natural gas. During extraction of hydrocarbon fuels (along with water) from extraction wells and transporting them to receiving facility such as but not limiting to onshore terminals, gas hydrates or clathrate hydrates are formed, which tend to clog the conveying lines including but not limiting to pipelines. To prevent the formation of gas hydrates (or clathrate hydrates), Mono Ethylene Glycol (MEG) is injected to the extraction well to form a mixture of hydrocarbon fuel and MEG. The presence of MEG prevents gas hydrate formation in the pipelines so that hydrocarbon fuels can be easily transported to the receiving facility. Once the mixture is received and collected, the hydrocarbon fuel is separated from the MEG. Then, MEG is regenerated to obtain a clear solution so that it can be injected back into extraction well to repeat the process.

The regeneration system disclosed in the present disclosure has two sections namely a pre-treatment section and a reclamation section. In pre-treatment section, the MEG is subjected to preliminary treatments to separate solid impurities like low solubility salts, and other fluidic impurities. This is to ensure that low solubility salts present in rich MEG are separated during initial stages of regeneration and they are not carried into the reclamation section. In reclamation section, other impurities such as high solubility salts and water are removed from rich MEG to obtain lean MEG, which is reused. The pre-treatment section comprises of a separation unit connected to the extraction well and adapted to receive well fluids which include mixture of fluidic hydrocarbon fuel and rich MEG. The separation unit separates the fluidic hydrocarbon fuel from the rich MEG. The hydrocarbon fuel is delivered to a dehydration unit for further processing, while the separated rich MEG is discharged into the pre-treatment section of the regeneration system. The pre-treatment section comprises of at least one flash drum which receives and accumulates rich MEG. In flash drum, fluidic impurities such as but not limiting to dissolved gases and hydrocarbon condensates are removed by altering physical variables of MEG, including but not limiting to temperature and pressure. The flash drum is fluidly connected to the separation unit. The rich MEG which is free from fluidic impurities is then routed to at least one settling tank fluidly connected to the flash drum. To the settling tank, chemicals are added, which convert low solubility salts present in the rich MEG into separable low solubility salt precipitates. The low solubility salt precipitates accummulate at the bottom of settling tank, with rich MEG remaining at the top. The low solubility salt precipitates containing traces of MEG is then routed to at least one filter unit which is fluidly connected downstream of the at least one settling tank. The filter unit separates low solubility precipitates from rich MEG by filtration. The filtrate containing rich MEG which is free from low solubility salts is then delivered to at least one storage tank fluidly connected downstream of the filter unit. The storage tank is configured to accummulate rich MEG and deliver it to the reclamation section of the regeneration system, where rich MEG is further processed to obtain lean MEG. The storage tank also has a separate outlet which is connected to the filter unit, so that the rich MEG stored in it can be circulated through the filter unit to carry out the filtration process multiple times. This is to minimize the concentration of low solubility salts in the rich MEG. In addition, the storage tank is also fluidly connected to the settling tank through an alternate line for receiving rich MEG directly from the settling tank. Accumulating rich MEG which has least concentration of low solubility salts in the at least one storage tank marks the end of pre-treatment of MEG.

The rich MEG stored in storage tank is routed to reclamation section of the regeneration system. The reclamation section essentially comprises of a reclamation column interchangeably referred to as distillation column which is fluidly connected to the storage tank. The reclamation column has a distillation chamber where water (or moisture) present in rich MEG is vaporized by varying its temperature. The vapours of water may still contain traces of MEG in mist state (in the form of minute droplets). To recover the MEG from vapours of water, the vapours are passed through a vane-mesh assembly. The vane-mesh assembly is positioned at an appropriate height inside the reclamation column and is basically designed to entrain minute (fine) solid impurities present in MEG vapors and water vapor. The vane-mesh assembly comprises of at least one vane pack and at least one mesh pack, each of which has a mesh configured to entrain fine solid particles, allowing the vapours to pass through them. In an embodiment of the disclosure, the vane pack and mesh pack entrain different sized particles since they have meshes with different sizes. The MEG is simultaneously circulated into at least one centrifuge which is fluidly connected to the reclamation column, while removal of water and fine solid particles is taking place. The centrifuge is configured to separate high solubility salts present in the MEG. The MEG so separated from high solubility salts is continuously re-circulated into the reclamation column to obtain lean MEG, which is taken out and reused. The water separated from rich MEG is discharged into effluent treatment plant for processing and salt particles separated from MEG in the centrifuge is disposed off. The regeneration system has water handling capacity from about 400 meter cube per day (m$^3$/day) to about 450 meter cube per day (m$^3$/day).

Use of terms such as "comprises", "comprising", or any other variations thereof in the description are intended to cover a non-exclusive inclusion, such that a setup system, device, assembly or method that comprises a list of components or steps does not include only those components or steps but may include other components or steps not expressly listed or inherent to such setup or device or system or method. In other words, one or more elements in a system or a mechanism proceeded by "comprising . . . a" does not, without more constraints, preclude the existence of other elements or additional elements in the system.

Reference will now be made to a system for regenerating mono ethylene glycol (MEG), and is explained with the help of figures. The figures are for the purpose of illustration only and should not be construed as limitations on the system. Wherever possible, referral numerals will be used to refer to the same or like parts.

FIG. 1 is an exemplary embodiment of the present disclosure which illustrates a system (100) for regenerating mono ethylene glycol (MEG). The system (100) is alternatively referred to as glycol pretreatment and reclamation plant throughout the specification. The system (100) is used to recover mono ethylene glycol, which is most commonly used as a hydrate inhibitor during extraction and processing of fossil fuels, and more specifically liquid and gaseous hydrocarbon fuels. During extraction and transportation of these fuels, pipelines are blocked due to the formation of gas hydrates or clathrate hydrates. These hydrates are in solid phase and are formed when non polar molecules (mostly gaseous molecules) are trapped in hydrogen bonded water molecules. Hence, the formation of gas hydrates in pipelines has to be avoided. To accomplish this, mono ethylene glycol (MEG) is added to the hydrocarbon fuel in the extraction well to form a mixture (well fluids). The mixture is transported to the receiving facility such as but not limiting to onshore terminals, where hydrocarbon fuel is separated from the MEG. The separated hydrocarbon fuel is processed further to dehydrate the gas, and thereafter to attain export specifications. On the other hand, the MEG separated from hydrocarbon fuel has impurities such as moisture, low solubility and high solubility salts, dissolved gases, hydrocarbon condensates and other solid and liquid impurities. Hence, pure MEG has to be recovered from these impurities, so that it can be re-injected into the extraction well for reuse. The regeneration of MEG is necessary due to high costs and complicated procedures involved during its synthesis (production).

As clearly shown in FIG. 1, well fluids, which essentially contain MEG, hydrocarbon fuel and other fluidic and solid impurities, are received at the receiving facility. The well fluids are stored in a reservoir including but not limiting to a tank, and are conveyed to a separation unit (200) fluidly connected to the reservoir. The separation unit (200) is configured to separate fluidic hydrocarbon fuel from the liquid MEG. The hydrocarbon fuel so separated is sent to dehydration unit for removing moisture content In an embodiment of the present disclosure, the separation unit (200) includes but not limiting to a slug catcher which separates gases from liquids in a two-phase flow stream by techniques, including but not limiting to gravity separation. The separated MEG is rich in water content and generally contains impurities in all three phases i.e. solid, liquid and gaseous phases, as mentioned in above paragraphs. Of these impurities, low solubility salts and high solubility salts are potential contaminants which tend to damage and/or choke pipelines and other components/units constituting the regeneration system (100). This MEG which is rich in water and salt is generally known as rich MEG. The water content present in rich MEG contains both formation water and condensation water. The formation water is formed as bi-product when MEG mixes with hydrocarbon fuel to form the mixture (or well fluids). Further, the formation water contains both low solubility salts and high solubility salts. Low solubility salts in formation water are mainly divalent salts including but not limiting to chlorides of Calcium, Iron and Magnesium. The presence of low solubility ions in rich MEG poses serious problems in the reclamation section (502). Hence, regeneration involves removing these impurities and water from rich MEG, to produce lean MEG, which can be reused.

The rich MEG is routed from the separation unit (200) to the pre-treatment section (501) of the regeneration system (100). The pre-treatment section (501) comprises of at least one flash drum (101) configured to receive rich MEG from the separation unit (200). The flash drum (101) is fluidly connected to the separation unit (200) and is configured to receive rich MEG from the separation unit (200). In flash drum (101), the rich MEG is subjected to variations in physical variables including but not limiting to temperature and pressure. Hence, dimensions and other design parameters including but not limiting to thermal stresses and stresses developed under fluid pressure are considered during flash drum (101) construction. The flash drum (101) also has auxiliary equipments (not shown) to bring about changes in physical variables of the rich MEG. For example, if a physical variable, such as temperature, of rich MEG is to be increased, auxiliary equipments such as but not limiting to heating coils may be employed. The above example is for the purpose of understanding only and is not in any way limiting the scope of the application. In an embodiment of the present disclosure, the geometry of the flash drum (101) includes but not limiting to cylindrical and spherical shapes or any polygonal shape.

The variation in physical variables cause fluidic impurities present in rich MEG to vaporize, leaving behind rich MEG containing water and other solid impurities. In an embodiment of the present disclosure, the fluidic impurities include but not limiting to dissolved gases such as but not limiting to hydrocarbon gases, and other condensates including but not liming to hydrocarbon condensates. In an exemplary embodiment, the fluidic impurities present in rich MEG are separated by heating the contents of the flash drum (101) to a temperature ranging from 75 degree celcius to 85 degree celcius (75° C. to 85° C.), and by reducing the pressure to 1.0 bar. In addition, increasing the temperature of rich MEG to a predetermined temperature range i.e. 75 degree celcius to 85 degree celcius accelerates the rate of reactivity of the low solubility salts in the settling tank (102). With the increase in rate of reactivity, the precipitation rate of low solubility salts into low solubility salt precipitates in the settling tank (102) increases. In another embodiment of the present disclosure, the fluidic impurities are separated from rich MEG by processes including but not limiting to fractional distillation, where impurities separate out as distillates due to difference in fractionating temperatures relative to that of rich MEG. The fluidic impurities so separated as vapours are let out of the flash drum (101) and may be recovered for other applications.

The rich MEG which is free from fluidic impurities is then delivered to at least one settling tank (102) which is fluidly connected to the at least one flash drum (101). The settling tank (102) receives rich MEG and accumulates it. The suspended and partially soluble impurities, corrosion particles and foreign particles present in rich MEG settle at the bottom of settling tank (102). The soluble impurities, and more particularly the inorganic salts which are ionic in nature, are carried by the hydrocarbon fuel from extraction wells during transportation. These salts are easily soluble in rich MEG owing to the presence of rich quantity of water in it. On the other hand, some of the salts which do not have affinity towards water remain as suspended impurities, which include but not limiting to sand and corrosion products.

The salts are mostly present in formation water and are commonly monovalent and divalent in nature. Monovalent salts include but not limiting to high solubility salts, and are generally ionic in nature. On the other hand, divalent salts include but not limiting to low solubility salts, such as but not limiting to chlorides of Calcium, Magnesium, Iron and the like. The presence of metallic cations render these salts partially soluble or less soluble, and cause problems such as scaling and corrosion in conveying lines, which eventually may lead to choking of these lines. This also results in sluggish operation and increases power consumption of the system (100). Hence, removal of divalent salts from rich MEG is desirable before MEG is passed into reclamation section (502) of the regeneration system (100).

The settling tank (102), which is fluidly connected to the at least one flash drum (101) allows rich MEG containing salts and other impurities to accumulate at its bottom. The settling tank (102) has at least one provision (not shown) through which chemical substances are added to the rich MEG. Addition of these chemical substances precipitate low solubility salts and causes the low solubility salt precipitates to accumulate at the bottom of the settling tank (102). While low solubility salt precipitates and corrosion products accumulate at the bottom of settling tank (102), the rich MEG containing water remains at the top portion of settling tank (102).

The pre-treatment section (501) further comprises of at least one filter unit (103) which is fluidly connected to the settling tank (102). The filter unit (103) is positioned downstream of the settling tank (102) and is adapted to receive rich MEG containing low solubility salt precipitates. The positioning of filter unit (103) on the downstream side of settling tank (102) is to facilitate easy flow of rich MEG and salt precipitates into it, through a slurry pump (not shown). The filter unit (103) has a first inlet (103*a*) fluidly connected to the settling tank (102) for receiving rich MEG containing low solubility precipitates. The filter unit (103), as is well known to a person skilled in the art, has at least one filtering medium, including but not limiting to semi-permeable membranes and mechanical filters. The size of particles retained or blocked by the filtering medium depends on its mesh size, which is usually lesser by several orders than the particle size. For example, a filtering medium with mesh size 10 microns can retain particles only with sizes greater than 10 microns and higher orders. Further, with decrease in mesh size of filtering medium, purity of the filtrate increases, which is due to detainment of more and more particles. To achieve better results, two or more filtering media with variation in mesh sizes may be placed adjacent to one another. One can use any filter unit (103) which is known in the art which can serve the purpose of removing divalent salt precipitates. In an embodiment of the present disclosure, the filter unit (103) includes but not limiting to a pressure assisted filter unit.

The filter unit (103) is intended to separate low solubility salt precipitates from the rich MEG flowing into it. The low solubility salt precipitates so separated are removed through a drain passage (103c) present in the filter unit (103) for disposal. The filtrate containing rich MEG, which is free from low solubility salt precipitates, is then routed for further processing. Further, as it can be seen in FIG. 1, the overflow passage (102a) of the settling tank (102) is also fluidly connected to the first inlet (103a) of the filter unit (103). This is to ensure that any traces of low solubility salt precipitates, which may still be present in rich MEG accumulated in the upper portion of settling tank (102), are filtered.

The filtrate containing rich MEG flowing out of the filter unit (103) is then discharged into at least one storage tank (104). The storage tank (104) is fluidly connected to the at least one filter unit (103) and is positioned downstream side of it. The filter unit (103) has an outlet (103d) through which the filtrate is discharged into the storage tank (104). In addition, the settling tank (102) shares a common path with the outlet (103d) of the filter unit (103), which is in fluid communication with the storage tank (104). The storage tank (104) receives rich MEG which is free from low solubility salts, from both the filter unit (103) and the settling tank (102), and stores it. The storage tank (104) also has a separate outlet which is fluidly connected to second inlet (103b) of the filter unit (103). This is to discharge rich MEG from the storage tank (104) to the filter unit (103) to achieve another stage of filtration so that traces of low solubility salts, which may still be present in rich MEG, are removed. The rich MEG stored in the storage tank (104) will be free from low solubility salt precipitates, but will have other impurities like high solubility salts, water content and other suspended particles.

The regeneration system (100) further comprises of a reclamation section (502) in fluid communication with the pre-treatment section. In reclamation section (502), water, high solubility salts and other impurities including but not limiting to solid particles are removed from rich MEG, so that lean MEG is recovered. The reclamation section (502) comprises of a reclamation column (105), at least one pump (109) and at least one centrifuge (108). The reclamation column (105) is fluidly connected to the storage tank (104), as shown in FIG. 1. The reclamation column (105) receives rich MEG form the storage tank (104) and is configured to remove water (moisture) and other solid impurities present in the rich MEG. The reclamation column (105) essentially comprises of a distillation chamber (106) and a vane mesh assembly (107) to perform the above mentioned process. In distillation chamber (106), the rich MEG is heated to predetermined temperature which causes water and MEG to vaporize. The temperature to which the rich MEG is heated depends on water concentration in the rich MEG. However, vaporized water and MEG will carry fine solid particles (impurities) with them, which are to be removed. To achieve this, a vane mesh assembly (107) is used. The vane mesh assembly (107) is explained in detail with reference to FIG. 2 in forthcoming paragraphs of detailed description. After removal of fine solid particles from vapours of water and MEG, vapours of water are separated from the MEG and purified MEG (lean MEG) is recovered. In an embodiment of the present disclosure, the recovery of MEG as lean MEG is achieved through processes including but not limiting to reflux, where lean MEG is recovered at the top of reclamation column (105) by stripping of MEG with reflux. In another embodiment of the present disclosure, lean MEG is recovered through processes including but not limiting to distillation and condensation. While the lean MEG is recovered, vapours of water exit out of the reclamation column (105) from its top which is condensed in top air cooler. The rich MEG supersaturated at bottom of reclamation column (105) and containing high solubility salts is simultaneously circulated into at least one centrifuge (108), which is fluidly connected to the reclamation column (106). The at least one pump (109), commonly referred to as recirculation pump is provided in the reclamation section (502), which is configured to draw rich MEG from the reclamation column (106) at suction pressure and deliver it to the centrifuge (108) at a predetermined delivery pressure. In an embodiment of the present disclosure, the pump includes but not limiting to recycle pump which can operate reversibly in the loop in which it is being used. In another embodiment of the present disclosure, the pump fluidly disposed between the centrifuge (108) and the reclamation column (105) includes but not limiting to mechanical, electrical and hydraulic pumps, such as but not limiting to centrifugal and axial flow pumps. The centrifuge (108) receives MEG and is configured to separate high solubility salts present in it. The basic principle of operation of a centrifuge (108), as is well known to a person skilled in the art, is separation of particles with differences in densities from another by subjecting them to centrifugal forces. For example, if separation of solid particles suspended in a liquid is to be carried out, the liquid is subjected to centrifugal forces. Solid particles, being denser than liquid molecules experience larger centrifugal force so that they are thrown outwards in the radial direction. This is carried out in a centrifuge (108). In an embodiment of the present disclosure, the centrifuge (108) is a decanter type centrifuge.

The centrifuge (108) separates high solubility salt particles which mostly include monovalent salts present in the MEG, by the principle of centrifugal reaction, as clearly explained above. The separated high solubility salts are disposed from the centrifuge (108) to effluent treatment plant [not shown] for appropriate treatments. The MEG separated from high solubility salts is recirculated to the reclamation column (106) so that distillation—mist and solid particle separation—high solubility salt separation processes take place in a continuous manner, generating lean MEG as the end product. In other words, the processes involved in transforming rich MEG into lean MEG in reclamation section (502) of the regenerating system (100) is a continuous process and has no predetermined sequence or antecedence.

In one embodiment of the present disclosure, the rich MEG flowing out of the storage unit (104) is subjected to distillation in the distillation chamber (106) of the reclamation column (105), where water (moisture) gets separated from rich MEG. This is followed by separation of fine solid impurities entrained in vapours of MEG and water by passing the vapours through the vane-mesh assembly (107).

In an alternate embodiment of the present disclosure, the rich MEG is directly circulated into the centrifuge (108) from the reclamation column (105) through at least one pump (109). After separation of high solubility salts from rich MEG, the rich MEG is recirculated to the reclamation column (105), where it is subjected to distillation (in distillation chamber (106)) to vaporize MEG and moisture present in it, followed by separation of fine solid impurities from vapours of MEG and water in the vane-mesh assembly (107), to obtain lean MEG. The term lean MEG used herein above and below refers to the form of MEG which is free from moisture and other soluble and insoluble impurities, having a concentration greater than 90% by weight, and with salinity less than 500 ppm. Mono Ethylene Glycol is suitable for re-injection into extraction well only if it is in the lean form.

Figure 2:
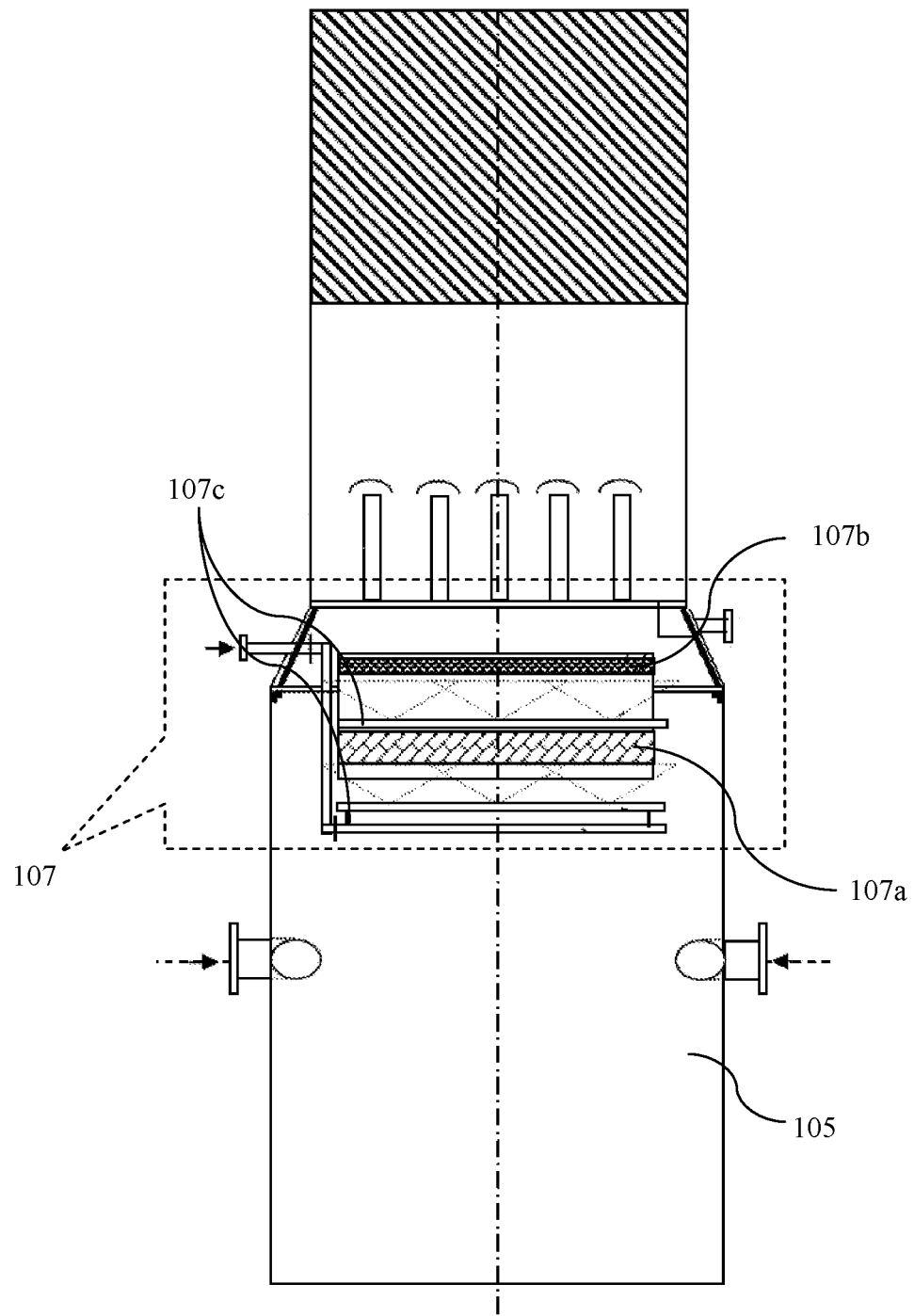
FIG. 2 illustrates schematic view of the vane mesh assembly used in distillation column of the system of FIG. 1, according to some embodiment of the present disclosure.

FIG. 2 is an exemplary embodiment of the present disclosure which illustrates schematic of the vane-mesh assembly (107) provided in the reclamation column (105). The vane-mesh assembly (107) comprises of a vane pack (107*a*) and a mesh pack (107*b*) which are configured to separate fine solid impurities. The basic difference between mesh pack (107*b*) and vane pack (107*a*) lies in the mesh size, and therefore, the size of particles trapped by them. The basic principle of operation of both mesh pack (107*b*) and vane pack (107*a*) is almost identical, and is as follows. The stream containing gases (or vapours) and fine solid particles is passed through a vane pack (107*a*) and a mesh pack (107*b*). The vapor/gas moves freely through the pores present in the vane or the mesh, without being trapped by them, while the fine solid particles come in contact with knitted wire surfaces and coalesce with them due to inertia. Depending on the size of each of vane pack (107*a*) and the mesh pack (107*b*), solid particles get entangled to the wire surfaces and thereby get separated from vapours of water and MEG. In an embodiment of the present disclosure, the vane pack (107*a*) used in the vane-mesh assembly (107) includes but not limiting to mellachevron vane pack and mesh pack (107*b*) includes but not limiting to knitmesh type mesh pack (107*b*).

In addition to separation of solid impurities from vapours of MEG and water, the vane-mesh assembly (107) also maintains the conductivity and salinity of MEG to desired levels to make it suitable for re-injection into the extraction well. This can be explained in an exemplary embodiment as follows: In the absence of vane-mesh assembly (107), the reclamation column (105) can handle water up to 250-300 meter cube per day (m$^3$/day). However, when an attempt was made to increase the water handling capacity of reclamation column (105), the conductivity of MEG became greater than 200 micro mhos and salinity of the MEG became greater than 500 ppm. The MEG with salinity greater than 500 ppm and conductivity greater than 200 micro mhos indicates a poor quality and is not suitable for re-injection into the extraction well. With the incorporation of vane-mesh assembly (107) in the reclamation column (105), salt particles are trapped by the vane pack (107*a*) and the mesh pack (107*b*), thereby reducing salinity of the MEG below 500 ppm, which in turn maintains the conductivity of the MEG below 200 micro mhos. This improves performance of the system (100), which in turn improves its efficiency and reduces power consumed per liter of MEG regenerated. In an exemplary embodiment of the present disclosure, the water handling capacity of the system (100) can be increased from 450 m$^3$/day to 500 m$^3$/day.

The vane-mesh assembly (107) of the reclamation column (105) is also provided with plurality of spray bars (107*c*) comprising spray nozzles configured to clean the vane pack (107*a*) and mesh pack (107*b*) by spraying a fluid under pressure. This has to be done periodically to remove solid particles tackled in the pores of both vane pack (107*a*) and mesh pack (107*b*), which otherwise would deteriorate the performance of both of them. Further, the presence of vane pack (107*a*) in the vane-mesh assembly (107) prevents fouling of the mesh pack (107*b*). The term "fouling" is defined as accumulation of unwanted matter including but not limiting to organic, inorganic and biological matter on solid surfaces, which is detrimental to their functioning. Fouling is prevented by the vane pack (107*a*) of the vane-mesh assembly (107) owing to its ability to retain large sized solid particles in the pores present in them. In an embodiment of the present disclosure, the size of particles that can be retained by vane pack (107*a*) of vane mesh assembly is greater than 20 microns, and size of particles that can be retained by pores of the mesh pack (107*b*) is greater than 10 microns.

In an exemplary embodiment of the present disclosure, the mesh pack (107*a*) is placed above the vane pack (107*b*), and the vane-mesh assembly (107) is positioned at a predetermined height in the reclamation column (107). According to this arrangement, the stream containing vapours of MEG and water with fine solid particles entrained in them initially passes through the vane pack (107*a*), where large sized solid impurities coalesce to wire mesh surfaces of the vane pack (107*a*), and are removed. Then the stream is passed through the mesh pack (107*b*) where carryover of fine salt particles with vapors of MEG and water is in the reclamation column (105) is prevented.

In an exemplary embodiment of the present disclosure, a method for regenerating mono ethylene glycol (MEG) is described with reference to FIG. 1. The method followed can be categorized into distinct steps or processes namely pre-treatment process and reclamation process. The pre-treatment process is carried out in pre-treatment section (501) of the system (100) and is aimed at separating low solubility salts from rich MEG. The sequence of steps involved in pre-treatment process is as follows. Firstly, the fluidic impurities present in rich mono ethylene glycol (MEG) are separated by supplying the rich mono ethylene glycol (MEG) to at least one flash drum (101), where the rich MEG is subjected to variations in physical variables including but not limiting to temperature and pressure. This is followed by routing the rich MEG to at least one settling tank (102) which is fluidly connected to the at least one flash drum (101). In settling tank (102), low solubility salts present in the rich mono ethylene glycol (MEG) are precipitated by adding chemical substances, and these low solubility salt precipitates are allowed to settle at the bottom of settling tank (102). The low solubility salt precipitates along with the rich mono ethylene glycol (MEG) are transported to at least one filter unit (103) which is fluidly connected to the downstream of at least one settling tank (102). The filter unit (103), as explained in above paragraphs, separates low solubility salt precipitates from the rich MEG. The filtrate containing rich mono ethylene glycol (MEG) (which is free from low solubility salts) flowing out of the at least one filter unit (103) is then routed to at least one storage tank (104) fluidly connected to downstream side of it. The storage tank (104) stores rich MEG which has impurities like water, high solubility salts and other solid impurities. This marks the end of pre-treatment process.

After completion of pre-treatment process, the rich MEG is routed to reclamation section (502) to perform reclamation process, where lean MEG is recovered from rich MEG. This involves following sequence of steps: The rich MEG stored in storage tank (104) is discharged into reclamation column (105) of reclamation section (502). In reclamation column (105), the rich MEG is subjected to distillation to separate water from it. The distillation process involves heating and vaporizing both water and rich MEG. The vapours of MEG as well as of water are passed through vane-mesh assembly (107) present in the reclamation column (105). In vane-mesh assembly (107), solid impurities present are separated by coalescence. Then, pure MEG (lean MEG) is recovered by any of the convenient methods as described in previous paragraphs, which involves separation of vapours of water from it. Simultaneously, the rich MEG accumulated at the bottom of reclamation column (105) and containing high solubility salts is routed into at least one centrifuge (108) by at least one pump (109). The high solubility salts are separated under centrifugal forces in the centrifuge (109). The MEG free from high solubility salts is re-circulated into reclamation column (105) so that the reclamation process takes place continuously, producing lean MEG as end product. By following above sequence of steps, the water handling capacity of reclamation section (502), and in turn the regenerating system (100) can be increased from about 400 m$^3$/day to about 450 m$^3$/day.

Advantages:

The present disclosure provides a system and method to regenerate mono ethylene glycol (MEG), in which the low solubility salts, and particularly divalent salts are removed by filtration in the pre-treatment section (in the filter unit). This reduces the tendency of choking the pipelines due to scale deposits and by impurities due to corrosion. This also reduces load on the centrifuge and increases its efficiency and durability, with minimum consumption of energy.

The present disclosure provides a system and method to regenerate mono ethylene glycol (MEG), in which low solubility salts, and specifically divalent salts are precipitated in settling tank by adding chemical substances. The precipitates can be easily removed by filtration, without the need for auxiliary powered devices to perform the same.

The present disclosure provides a system and method to regenerate mono ethylene glycol (MEG), in which the vane mesh assembly maintains salinity and conductivity of the MEG to desired values and makes it suitable for re-injecting to the extraction well.

The present disclosure provides a system and a method to regenerate mono ethylene glycol (MEG), in which the arrangement of pre-treatment section and reclamation section increases overall efficiency of the system, as well as water handling capacity of the system from about 400 m$^3$/day to about 450 m$^3$/day.

The present disclosure provides a system and method to regenerate mono ethylene glycol (MEG), in which the purity of lean MEG recovered from rich MEG is high (about 90% wt with salinity less than 500 ppm). This is attributed to the presence of filter unit in pre-treatment section and vane-mesh assembly in reclamation section.

EQUIVALENTS

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

INDUSTRIAL APPLICABILITY

The system for regenerating mono ethylene glycol and method for the same can be used in the extraction of fossil fuels including but not limiting to natural gas and petroleum. Mono ethylene glycol is added to prevent hydrate formation during extraction and transportation of these fossil fuels, and is regenerated at the receiving facility by the system and by following the method as described throughout the specification.

| Table of Referral Numerals: | |
|---|---|
| Reference Number | Description |
| 100 | System for regenerating mono ethylene glycol |
| 200 | Separation unit |
| 101 | Flash drum |
| 102 | Settling tank |
| 102a | Overflow passage of settling tank |

-continued

Table of Referral Numerals:

| Reference Number | Description |
| --- | --- |
| 103 | Filter unit |
| 103a and 103b | First and second inlets of filter unit |
| 103c | Drain passage of filter unit |
| 103d | Outlet of filter unit |
| 104 | Storage tank |
| 105 | Reclamation column |
| 106 | Distillation chamber |
| 107 | Vane-mesh assembly |
| 107a | Vane pack |
| 107b | Mesh pack |
| 107c | Spray bars/nozzles |
| 108 | Centrifuge |
| 109 | Pump |
| 501 | Pre-treatment section |
| 502 | Reclamation section |

We claim:

1. A system for regenerating Mono Ethylene Glycol (MEG), the system comprising:
at least one flash drum adapted to receive rich mono ethylene glycol (MEG), wherein the rich mono ethylene glycol (MEG) is heated to a predetermined temperature in the at least one flash drum;
at least one settling tank fluidly connected to the at least one flash drum, wherein low solubility salts present in the rich mono ethylene glycol (MEG) are precipitated in the at least one settling tank;
at least one filter unit fluidly connected to the at least one settling tank, wherein the at least one filter unit is positioned downstream of the at least one settling tank and is configured to separate low solubility salt precipitates from the rich mono ethylene glycol (MEG);
at least one storage tank positioned downstream of the at least one filter unit, wherein the at least one storage tank is configured to receive and accumulate filtrate containing rich mono ethylene glycol (MEG) flowing out of the filter unit;
a reclamation column fluidly connected to the at least one storage tank, the reclamation column comprising:
a distillation chamber configured to vaporize water present in the rich mono ethylene glycol (MEG) to produce lean mono ethylene glycol (MEG); and
a vane-mesh assembly configured to separate fine solid particles from the vaporized mono ethylene glycol (MEG) and water;
at least one centrifuge fluidly connected to the reclamation column, wherein the at least one centrifuge is configured to separate high solubility salts from the mono ethylene glycol (MEG),
wherein, the system is configured to handle water from 400 meter cube per day ($m^3$/day) to 450 meter cube per day ($m^3$/day).

2. The system as claimed in claim 1, wherein the mono ethylene glycol (MEG) is used as hydrate inhibitor during processing of liquid and gaseous hydrocarbon fuels.

3. The system as claimed in claim 1 comprises of at least one separation unit fluidly connected to the at least one flash drum and configured to separate hydrocarbon fuel from rich mono ethylene glycol (MEG).

4. The system as claimed in claim 1, wherein the predetermined temperature ranges from 75 degree celcius (° C.) to 85 degree celcius (° C.).

5. The system as claimed in claim 1, wherein the at least one settling tank comprises of at least one overflow passage to allow flow of rich mono ethylene glycol (MEG) into the filter unit.

6. The system as claimed in claim 1, wherein the at least one settling tank comprises of at least one provision to receive chemical substances.

7. The system as claimed in claim 6, wherein the chemical substances convert low solubility salts present in the rich mono ethylene glycol (MEG) into low solubility salt precipitates.

8. The system as claimed in claim 1, wherein the at least one filter unit comprises of a first inlet fluidly connected to bottom of the at least one settling tank.

9. The system as claimed in claim 1, wherein the at least one filter unit comprises of a second inlet fluidly connected to the at least one storage tank.

10. The system as claimed in claim 1, wherein the at least one filter unit comprises of a drain passage configured to discharge low solubility salt precipitates.

11. The system as claimed in claim 1, wherein the at least one settling tank is fluidly connected to the at least one storage tank.

12. The system as claimed in claim 1, wherein the vane-mesh assembly comprises of at least one vane pack and at least one mesh pack configured to filter the fine solid particles from the mono ethylene glycol (MEG).

13. The system as claimed in claim 12, wherein the at least one vane pack of the vane-mesh assembly filters solid particles of size greater than 20 microns.

14. The system as claimed in claim 12, wherein the at least one mesh pack of the vane-mesh assembly filters solid particles of size greater than 10 microns.

15. The system as claimed in claim 1 comprises of at least one pump fluidly disposed between the reclamation column and the at least one centrifuge.

16. The system as claimed in claim 15, wherein the at least one pump is configured to circulate the rich mono ethylene glycol (MEG) between the reclamation column and the at least one centrifuge.

17. The system as claimed in claim 1, wherein the water vaporized in reclamation column is discharged to effluent treatment plant.

18. A method for regenerating mono ethylene glycol (MEG), the method comprising acts of:
increasing temperature of rich mono ethylene glycol (MEG) by heating the rich mono ethylene glycol (MEG) in at least one flash drum;
precipitating low solubility salts present in the rich mono ethylene glycol (MEG) in at least one settling tank, wherein the at least one settling tank is fluidly connected to the at least one flash drum;
separating low solubility salt precipitates from the rich mono ethylene glycol (MEG) in at least one filter unit, wherein the at least one filter unit is fluidly connected to the at least one settling tank and is positioned downstream of the at least one settling tank;
accumulating filtrate containing rich mono ethylene glycol (MEG) flowing out of the at least one filter unit in at least one storage tank, wherein the at least one storage tank is fluidly connected to the at least one filter unit and is positioned downstream of the at least one filter unit; and
routing the filtrate containing rich mono ethylene glycol (MEG) from the at least one storage tank to a reclamation column to obtain lean mono ethylene glycol (MEG), wherein obtaining the lean mono ethylene glycol (MEG) from the reclamation column comprises steps of:
- separating high solubility salts from the rich mono ethylene glycol (MEG) by at least one centrifuge fluidly connected to the reclamation column;
- vaporizing water present in the rich mono ethylene glycol (MEG) in a distillation chamber of the reclamation column; and
- separating fine solid particles from the vaporized mono ethylene glycol (MEG) and water through a vane-mesh assembly of the reclamation column;

wherein, the system is configured to handle water from 400 meter cube per day ($m^3$/day) to 450 meter cube per day ($m^3$/day).

19. The method as claimed in claim 18, wherein the rich mono ethylene glycol (MEG) is heated to a temperature ranging from 75 degree celcius (° C.) to 85 degree celcius (° C.) in the at least one flash drum.

20. The method as claimed in claim 18, wherein the separation of high solubility salts and vaporization of water occur simultaneously.

21. The method as claimed in claim 18 comprises act of separating hydrocarbon fuel from the rich mono ethylene glycol (MEG) in at least one separation unit fluidly connected to the flash drum.

22. The method as claimed in claim 18, wherein increasing the temperature of rich mono ethylene glycol (MEG) facilitates precipitation of low solubility salts in the settling tank and separation of fluidic impurities from the rich mono ethylene glycol (MEG).

23. The method as claimed in claim 18 comprises act of routing excess rich mono ethylene glycol (MEG) from the at least one settling tank to the at least one filter unit through at least one overflow passage.

24. The method as claimed in claim 18 comprises act of routing rich mono ethylene glycol (MEG) from the at least one storage tank to the at least one filter unit through at least one port.

25. The method as claimed in claim 18, wherein the low solubility precipitates are formed by adding chemical substances to rich mono ethylene glycol (MEG) in the at least one settling tank.

* * * * *